United States Patent [19]

Maier

[11] 4,213,922

[45] Jul. 22, 1980

[54] PROCESS FOR PRODUCING PHOSPHONIC ACID HALIDES

[75] Inventor: Ludwig Maier, Arlesheim, Switzerland

[73] Assignee: Ciba-Geigy Corporation, Ardsley, N.Y.

[21] Appl. No.: 944,232

[22] Filed: Sep. 20, 1978

Related U.S. Application Data

[63] Continuation-in-part of Ser. No. 880,904, Feb. 24, 1978, abandoned.

[51] Int. Cl.$^2$ .......................... C07F 9/146; C07F 9/38
[52] U.S. Cl. ............................... 260/958; 260/543 P; 260/955; 260/960
[58] Field of Search .................... 260/544 P, 955, 958, 260/960, 543 P

[56] References Cited

U.S. PATENT DOCUMENTS

| | | | |
|---|---|---|---|
| 2,847,469 | 8/1958 | Dawson et al. | 260/543 P |
| 3,972,923 | 8/1976 | Finke et al. | 260/543 P |

OTHER PUBLICATIONS

Syn. Recc. Inorg. Metal Org. Chem. vol. 4, p. 417 (1974).
Kittila, "Dimethyl Formamide Chemical Uses", pp. 76-85 (1967).

*Primary Examiner*—Norman Morgenstern
*Attorney, Agent, or Firm*—Harry Falber

[57] ABSTRACT

Phosphonic acid halides are prepared by reacting a dialkylphosponate with thionyl chloride or thionyl bromide in the presence of a nitrogen compound from the group comprising N,N-disubstituted formamides, tertiary amines and N,N-disubstituted phosphoric acid triamides. Phosphonic acid dihalides as well as phosphonic acid alkylester monohalides can be prepared by the new process.

8 Claims, No Drawings

PROCESS FOR PRODUCING PHOSPHONIC ACID HALIDES

This application is a continuation-in-part of application Ser. No. 880,904, filed Feb. 24, 1978, now abandoned.

The present process relates to a process for producing phosphonic acid halides of the formula I $$R-P\begin{matrix}O\\\parallel\\\phantom{P}\end{matrix}\begin{matrix}X_1\\ \\X_2\end{matrix} \qquad (I)$$

in which
- R represents a straight-chain or branched-chain alkyl group which has 1 to 12 carbon atoms and which can be mono- to trisubstituted by fluorine, chlorine or bromine, and mono- or disubstituted by a phenyl group unsubstituted or substituted by fluorine, chlorine or bromine or by an alkyl group having 1 to 12 carbon atoms, or represents a cycloalkyl group which has 4 to 6 ring carbon atoms and which can be substituted by alkyl having 1 to 5 carbon atoms, and/or bound by an alkylene group having 1 to 4 carbon atoms, or R represents a phenyl group unsubstituted or substituted by fluorine, chlorine or bromine or by alkyl having 1 to 5 carbon atoms,
- $X_1$ represents chlorine or bromine, and
- $X_2$ represents an alkoxy group having 1 to 12 carbon atoms, chlorine or bromine.

Alkylphosphonic acid halides of the formula I are valuable intermediates. They can be converted for example by reaction with various hydroxyl and mercapto compounds into alkylphosphonates or alkylthiophosphonates, with the esters obtained by reaction with polyhydric alcohols, such as glycerol, trimethylpropane, 2,2-dimethylpropane-1,3-thiol or pentaerythritol, being used principally as flameproofing agents, whereas the reaction with alkanols, alkylmercaptans, phenols and thiophenols yields above all phosphonates which have an insecticidal action.

It has already been suggested to produce alkylphosphonic acid dichlorides by reaction of dialkyl alkylphosphonates with thionyl chloride. There is thus known for example from the U.S. Pat. No. 2,847,469 a process in which the reaction of a dialkyl alkylphosphonate with thionyl chloride is performed at temperatures of 130° to 200° C. in a packed column by passing the dialkyl alkylphosphonate in a direction counter to the flow of the thionyl chloride vapours rising in the column. Notwithstanding a relatively large expenditure on apparatus, this process produces the desired alkylphosphonic acid dichlorides in a yield merely of 80% of theory.

According to a further process, described in Syn. React. Inorg. Metal Org. Chem. 4, 417 (1974), for producing methyl phosphonic acid dichlorides, the reaction of dimethyl methylphosphonate with thionyl chloride is performed by adding dropwise the dimethyl methylphosphonate very slowly to boiling thionyl chloride, and refluxing for about 15 hours the mixture obtained after completion of the addition of the dimethyl methylphosphonate. According to the authors, methylphosphonic acid dichloride is obtained in a yield of 98% of theory. The applicability of the process is limited however to the production of methylphosphonic acid dichloride, for even ethylphosphonic acid dichloride is obtained using this method in a yield of only 72% of theory, whilst β-chloroethylphosphonic acid dichloride and butylphosphonic acid dichloride cannot be produced at all in this manner. The production of methylphosphonic acid dichloride too by this process is not however without problems, for on working according to the instructions given in the aforesaid publication, methylphosphonic acid dichloride could be obtained in a yield of only 25 to 50% of theory. A further disadvantage of the process has to be seen in the very long reaction times.

It is therefore the object of the present invention to provide, on the basis of the reaction of phosphonates with thionyl halides, a generally applicable process for producing phosphonic acid halides of the formula I, by means of which these compounds can be produced in good yields with short reaction times.

It has been found that phosphonic acid halides of the formula I are obtained in excellent yields by reacting a dialkylphosphonate of the formula II $$R-P\begin{matrix}O\\\parallel\\\phantom{P}\end{matrix}\begin{matrix}O\,Alk\\ \\O\,Alk\end{matrix} \qquad (II)$$

wherein R has the meaning given under the formula I, and "Alk" represents an alkyl group having 1 to 12 carbon atoms, at 70° to 150° C., in the presence of 0.005 to 0.05 mol, per mol of dialkylphosphonate of the formula II, of a nitrogen compound from the group comprising N,N-disubstituted formamides, tertiary amines and N,N-disubstituted phosphoric acid triamides with at least the equivalent amount of a thionyl halide of the formula III $$SO(Hal)_2 \qquad (III)$$

in which "Hal" represents chlorine or bromine.

Suitable N,N-disubstituted formamides are those which are substituted on the nitrogen atom by lower alkyl groups or by a lower alkyl group and a phenyl group or by two phenyl groups, with two alkyl groups being able to form a polymethylene group which can be interrupted by an oxygen atom and which forms with the adjacent nitrogen atom a heterocyclic ring. Particularly suitable N,N-disubstituted formamides correspond to the formula IV $$H-\overset{O}{\overset{\parallel}{C}}-N\begin{matrix}R_1\\ \\R_2\end{matrix} \qquad (IV)$$

in which $R_1$ and $R_2$ independently of one another each represent an alkyl group having 1 to 5 carbon atoms, a phenyl group or, together with the adjacent nitrogen atom, a pyrrolidino, piperidino or morpholino group. The following may be mentioned as examples of particularly suitable N,N-disubstituted formamides of the formula IV: N,N-dimethylformamide, N,N-diethylformamide, N-methyl-N-ethylformamide, N,N-dipropylformamide, N,N-dibutylformamide, N-phenyl-N-methylformamide, N-formylpyrrolidine, N-formylpiperidine and N-formylmorpholine. An especially suitable N,N-disubstituted formamide of the formula IV is N,N-dimethylformamide.

Suitable tertiary amines are trialkylamines, N,N-dialkylarylamines, pyridine and N',N'-dialkylaminopyridines, with in each case two alkyl groups being able to form a polymethylene group which can be interrupted by an oxygen atom and which forms with the nitrogen a heterocyclic ring. Particularly suitable tertiary amines correspond to the formula V $$A-R_3 \quad (V)$$

in which $R_3$ represents an alkyl group having 1 to 4 carbon atoms, a phenyl group or a 2-, 3- or 4-pyridyl group and A represents a dialkylamino group $-N-R_4R_5$, in which $R_4$ and $R_5$ independently of one another each represent an alkyl group having 1 to 4 carbon atoms, and the two alkyl groups $R_4$ and $R_5$ together with the nitrogen atom can form a pyrrolidino, piperidino or morpholino group, and if $R_3$ represents a pyridyl group A can also represent hydrogen.

Examples which may be mentioned of particularly suitable tertiary amines are: trimethylamine, triethylamine, tripropylamine, tributylamine, N,N-dimethylaniline, N,N-diethylaniline, pyridine, N',N'-dimethylaminopyridine, N-methylpyrrolidine, N-methylpiperidine and N-morpholine.

Suitable N,N-disubstituted phosphoric acid triamides are hexaalkylphosphoric acid triamides, and in each case the two alkyl groups bound to a nitrogen atom can form a polymethylene group which can be interrupted by an oxygen atom and which forms with the nitrogen atom a heterocyclic ring. Especially suitable N,N-disubstituted phosphoric acid triamides correspond to the formula VI

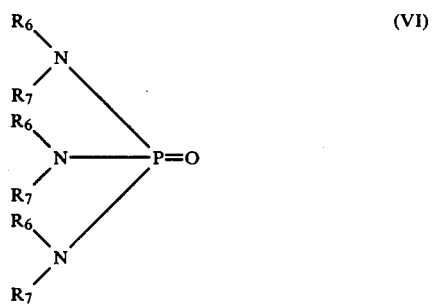

(VI)

in which $R_6$ and $R_7$ each represent an alkyl group having 1 to 3 carbon atoms, or in each case form, together with the nitrogen atom, a pyrrolidino, piperidino or morpholino ring.

The following may be mentioned as examples of particularly suitable N,N-disubstituted phosphoric acid triamides: hexamethylphosphoric acid triamide, hexaethylphosphoric acid triamide, phosphoric acid tripyrrolidide, phosphoric acid tripiperidide and phosphoric acid trimorpholidide.

The reaction of a dialkylphosphonate of the formula II with a thionyl halide of the formula III can be performed in the presence or absence of an inert organic solvent. Suitable solvents are for example aromatic hydrocarbons such as toluene and xylene, halogenated aromatic hydrocarbons such as chlorobenzene and o-dichlorobenzene, aliphatic hydrocarbons having a boiling point between 120° and 140° C., such as high-boiling petroleum ether, octane and nonane, and halogenated aliphatic hydrocarbons such as trichloroethane and tetrachloroethane. Also excess thionyl halide can serve as solvent.

There are used per mol of phosphonate of the formula II at least 2 mols of thionyl halide. The molar ratio of the phosphonate of the formula II to thionyl halide of the formula III is preferably 1:2.2 to 2.5. It is possible to use a larger excess of thionyl halide, but this offers no advantage.

The amount of nitrogen compound, in the presence of which the reaction of a phosphonate of the formula II with a thionyl halide of the formula III is performed, is according to the invention between 0.005 and 0.05 mol per mol of the phosphonate of the formula II. Smaller or larger amounts of the nitrogen compound have a disadvantageous effect on the yield of phosphonic acid halide of the formula I.

Suitable thionyl halides of the formula III are thionyl chloride and thionyl bromide; thionyl chloride is preferably used.

The reaction of a phosphonate of the formula II with a thionyl halide of the formula III is performed according to the invention at temperatures between 80° and 150° C. The temperature range of between 80° and 120° C. is passed through when, using a preferred variant of the process according to the invention, a phosphonate of the formula II is reacted with 2.2 to 2.5 mols of thionyl chloride in the presence of 0.005 to 0.05 mol of dimethylformamide, and the reaction mixture is maintained continuously at the reflux temperature. With the reaction of phosphonates of the formula I which are slow to react, for example in the case of the reaction of β-halogenoethylphosphonates, it can be of advantage to perform the reaction at 130° to 150° C. in a closed system.

The reaction times are as a rule between 1 and 20 hours depending on the reaction temperature and on the reactivity of the components used. In certain cases, where starting materials which are particularly slow to react are used, longer reaction times may be necessary. For example, the reaction of O,O-bis-(β-chloroethyl)-phosphonate with 2 mols of thionyl chloride at a reaction temperature of 80° to 110° C. to give O-(β-chloroethyl)-β-chloroethylphosphonic acid chloride requires about 70 hours. The reaction of the second β-chloroethoxy group is performed preferably at 130° to 150° C. in an autoclave.

The processing of the reaction mixture can be carried out, depending on whether the final products are liquid or solid, by distillation or crystallisation. After separation by distillation of the solvent and/or of the unreacted thionyl halide, the products formed are as a rule sufficiently pure to render further purification unnecessary.

As alkyl groups, the radicals R and $X_2$ in the formula I can be straight-chain or branched-chain. The radical R as a substituted or unsubstituted phenyl group can be mono- to pentasubstituted by fluorine, chlorine or bromine or by an alkyl group having 1 to 5 carbon atoms.

The process according to the invention is suitable for producing phosphonic acid dihalides of the formula I, which for their part are valuable intermediates. Compared with known processes, the process according to the invention is distinguished by its general applicability. A further advantage of the process according to the invention is that it can be performed in stages, and is therefore suitable also for producing phosphonic acid ester monohalides.

The process according to the invention is further illustrated by the Examples which follow.

EXAMPLE 1

Methylphosphonic acid dichloride

A mixture of 124 g (1 mol) of O,O-dimethyl-methylphosphonate and 0.73 g (0.01 mol) of dimethylformamide is added dropwise at reflux temperature, in the course of 2 hours, to 297.5 g (2.5 mols) of thionyl chloride. An intense gas-generation of sulfur dioxide and methyl chloride occurs during the dropwise addition. After completion of the addition, stirring is maintained for 7½ hours at reflux temperature. Unreacted thionyl chloride is subsequently evaporated off at 25° C. in a water-jet vacuum. There is obtained in this manner 133.1 g (100.2% of theory) of crude methylphosphonic acid dichloride, which crystallises completely on standing at room temperature and melts at 33° C. Distillation of the crude product at 56° to 57° C. and 14 Torr yields 125.5 g (94.4% of theory) of pure methylphosphonic acid dichloride having a melting point of 33° C.

The reaction of dimethyl methylphosphonate (DMP) is performed in an analogous manner with differing amounts of thionyl chloride in the presence of various nitrogen compounds of which the amounts are likewise varied. The following nitrogen compounds are used:
(a) N,N-dimethylformamide,
(b) N-formylmorpholine,
(c) N-formylpiperidine,
(d) N-formylpyrrolidone,
(e) triethylamine,
(f) pyridine,
(g) 4-dimethylaminopyridine, and
(h) hexamethylphosphoric acid triamide.

The test results are summarised in the following Table.

| Molar ratio $SoCl_2$:DMP | Nitrogen compound | Mols of nitrogen compound per mol of DMP | Dropwise addition time [h] | Subsequent stirring time [h] | Final temperature [°C.] | Net yield [% of theory] |
| --- | --- | --- | --- | --- | --- | --- |
| 2,5:1 |   | 0 | 4 | 15 | 80 | 47,3 |
| 2,5:1 | — | 0 | 4 | 35 | 80 | 50,0 |
| 2,1:1 | a | 0,001 | 1½ | 1 |   | 24,0 |
| 2,1:1 | a | 0,005 | 4 | 3 | 130 | 76,5 |
| 2,1:1 | a | 0,01 | 1 | 4,5 | 130 | 68,5 |
| 2,2:1 | a | 0,05 | 2 | 1,5 | 130 | 71,0 |
| 2,2:1 | a | 0,1 | 2 | 1 | 140 | 58,7 |
| 2,5:1 | a | 0,01 | 4 | 15 | 120 | 93,0 |
| 2,5:1 | a | 0,01 | 2 | 7,5 | 120 | 94,4 |
| 2,5:1 | a | 0,05 | 2 | 0 | 110 | 76,6 |
| 2,5:1 | a | 0,005 | 2 | 10,5 | 110 | 91,4 |
| 2,5:1 | a | 0,001 | 2 | 7,0 | 110 | 23,8 |
| 2,5:1 | a | 0,01 | 2 | 7,0 | 110 | 95,9 |
| 2,5:1 | b | 0,01 | 2 | 19 |   | 96,0 |
| 2,5:1 | c | 0,01 | 2 | 19 |   | 99,2 |
| 2,5:1 | d | 0,01 | 2 | 19 |   | 91,0 |
| 2,3:1 | e | 0,01 | 2 | 11 |   | 83,5 |
| 2,3:1 | f | 0,01 | 2 | 8 |   | 91,2 |
| 2,3:1 | g | 0,01 | 2 | 9,5 |   | 91,3 |
| 2,3:1 | h | 0,01 | 2 | 11,5 |   | 92,9 |

EXAMPLE 2

Ethylphosphonic acid dichloride

A mixture of 166.1 g (1 mol) of O,O-diethyl-ethylphosphonate and 1.46 g (0.02 mol) of dimethylformamide is added dropwise at reflux temperature, in the course of 5 hours, to 297.5 g (2.5 mols) of thionyl chloride. There occurs during the addition an intense gas-generation of sulfur dioxide and ethyl chloride. As is shown by a $^1$H-NMR spectrographic examination, pure ethylphosphonic acid ethyl ester chloride is present after completed addition of the diethyl-ethylphosphonate. The reaction mixture is subsequently stirred for 18 hours at reflux temperature, and is then freed in a water-jet vacuum at 25° C. from unreacted thionyl chloride to leave 147 g (100% of theory) of crude ethylphosphonic acid dichloride. The crude product is purified by vacuum distillation to yield 140.8 g (95.8% of theory) of pure ethylphosphonic acid dichloride; boiling point 67° to 68° C./13 Torr.

EXAMPLE 3

O-(β-chloroethyl)-β-chloroethylphosphonic acid chloride

A mixture of 142.7 g (0.53 mol) of O,O-(β-chloroethyl)-β-chloroethylphosphonate and 1.1 g (0.03 mol) of dimethylformamide is added dropwise at reflux temperature, in the course of 3 hours, to 148.7 g (1.25 mols) of thionyl chloride. After the addition is completed, the reaction mixture is kept at reflux temperature until the generation of sulfur dioxide ceases, which is the case after about 70 hours. Fraction distillation of the reaction mixture yields, after first runnings, 99 g (82.8% of theory) of O-(β-chloroethyl)-β-chloroethylphosphonic acid chloride having a boiling point of 157° to 162° C./0.5 Torr, which, after repeated distillation, boils constant at 109° to 110° C./0.15 Torr.

EXAMPLE 4

β-Chloroethylphosphonic acid dichloride

A mixture of 142.7 g (0.53 mol) of O,O-(β-chloroethyl)-β-chloroethylphosphonate and 1.8 g (0.05 mol) of dimethylformamide is added dropwise at reflux temperature, in the course of 3 hours, to 148.7 g (1.25 mols) of thionyl chloride. After completion of the addition, the reaction mixture is firstly held for 22 hours at reflux temperature, and is then heated for 10 hours at 135° C. in a bomb tube. Fractional distillation of the reaction mixture yields 33.7 g (34.6% of theory) of β-chloroethylphosphonic acid dichloride having a boiling point of 111° to 115° C./15 Torr, and 11.2 g (5% of theory) of O-(β-chloroethyl)-β-chloroethylphosphonic acid chloride.

EXAMPLE 5

O-Methyl-methylphosphonic acid chloride

A mixture of 134.8 g (1 mol) of dimethyl-methylphosphonate and 0.73 g (0.01 mol) of dimethylformamide is added dropwise at reflux temperature, in the course of 2 hours, to 297.5 g (2.5 mols) of thionyl chloride. After completion of the addition, the reaction mixture is held for a further half hour at reflux temperature. Subsequent vacuum distillation yields 38.5 g (30% of theory) of O-methyl-methylphosphonic acid chloride having a boiling point of 78° to 82° C./14 Torr. The losses in yield occurring in processing are to be attributed to the fact that the O-methyl-methylphosphonic acid chloride present originally in virtually the pure form polymerises with the splitting-off of methyl chloride.

EXAMPLE 6 n-Dodecylphosphonic acid dichloride

A mixture of 52.8 g (0.172 mol) of diethyl n-dodecylphosphonate and 0.126 g (0.00172 mol) of dimethylformamide is added dropwise within 2 hours to 51.3 g (0.516 mol) of boiling thionyl chloride. The reaction mixture is maintained for a further 26.5 hours at boiling temperature and is subsequently processed by fractional distillation to yield 39.7 g (81% of theory) of pure n-dodecylphosphonic acid dichloride having a boiling point of 128° to 130° C./0.3 Torr.

EXAMPLE 7

Phenylphosphonic acid dichloride

A mixture of 21.4 g (0.1 mol) of diethyl-phenylphosphonate and 0.113 g (0.001 mol) of N-formylpiperidine is added dropwise during 2 hours to 18.2 ml (0.25 mol) of boiling thionyl chloride. After completion of the addition, the reaction mixture is kept for a further 20 hours at reflux temperature, and is subsequently processed by fractional distillation to yield 17.8 g (91.3% of theory) of pure phenylphosphonic acid dichloride having a boiling point of 132° to 136° C./18 Torr.

I claim:

1. A process for producing phosphonic acid halides of the formula

(I)

in which
R represents a straight-chain or branched-chain alkyl group which has 1 to 12 carbon atoms and which can be mono- to trisubstituted by fluorine, chlorine or bromine, and mono- or disubstituted by a phenyl group unsubstituted or substituted by fluorine, chlorine or bromine or by an alkyl group having 1 to 12 carbon atoms, or represents a cycloalkyl group which has 4 to 6 ring carbon atoms and which can be substituted by alkyl having 1 to 5 carbon atoms, or bound by an alkylene group having 1 to 4 carbon atoms, or R represents a phenyl group which is unsubstituted or substituted by fluorine, chlorine or bromine or by alkyl having 1 to 5 carbon atoms,
$X_1$ represents chlorine or bromine, and
$X_2$ represents an alkoxy group having 1 to 12 carbon atoms, chlorine or bromine, which process comprises reacting a dialkylphosphonate of the formula II

wherein R has the meaning given under the formula I, and "Alk" represents an alkyl group having 1 to 12 carbon atoms, at 70° to 150° C., in the presence of 0.005 to 0.05 mol, per mol of dialkylphosphonate of the formula II, of a nitrogen compound selected from the group consisting of
(1) N,N-disubstituted formamides which are substituted on the nitrogen atom by lower alkyl groups or by a lower alkyl group and a phenyl group or by two phenyl groups, with two alkyl groups being able to form a polymethylene group which can be interrupted by an oxygen atom and which forms with the adjacent nitrogen atom a heterocyclic ring;
(2) tertiary amines selected from the group consisting of trialkylamines, N,N-dialkyl-arylamines, pyridine and N',N'-dialkylaminopyridine, with in each case two alkyl groups being able to form a polymethylene group which can be interrupted by an oxygen atom and which forms with the nitrogen atom a heterocyclic ring; and
(3) N,N-disubstituted phosphoric acid triamides selected from the group consisting of hexa-alkylphosphoric acid triamides, with in each case the two alkyl groups bound to a nitrogen atom being able to form a polymethylene group which can be interrupted by an oxygen atom and which forms with the nitrogen atom a heterocyclic ring;
with at least the equivalent amount of a thionyl halide of the formula III

SO(Hal)$_2$ (III)

in which "Hal" represents chlorine or bromine.

2. A process according to claim 1, wherein the nitrogen compound used is an N,N-disubstituted formamide of the formula IV

(IV)

in which $R_1$ and $R_2$ independently of one another each represent an alkyl group having 1 to 5 carbon atoms, a phenyl group or, together with the adjacent nitrogen atom, a pyrrolidino, piperidino or morpholino group.

3. A process according to claim 1, wherein the nitrogen compound used is N,N-dimethylformamide.

4. A process according to claim 1, wherein the nitrogen compound used is a tertiary amine of the formula V

A—R$_3$ (V)

in which R$_3$ represents an alkyl group having 1 to 4 carbon atoms, a phenyl group or a 2-, 3- or 4-pyridyl group and A represents a dialkylamino group —N—R$_4$R$_5$, in which R$_4$ and R$_5$ independently of one another each represent an alkyl group having 1 to 4 carbon atoms, with the two alkyl groups $R_4$ and $R_5$ together with the nitrogen atom being able to form a pyrrolidino, piperidino or morpholino group, and if $R_3$ represents a pyridyl group A can also represent hydrogen.

5. A process according to claim 1, wherein the nitrogen compound used is an N,N-disubstituted phosphoric acid triamide of the formula VI

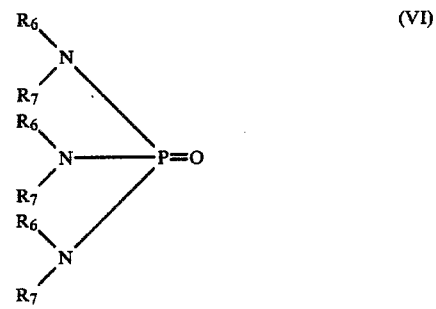

in which $R_6$ and $R_7$ each represent an alkyl group having 1 to 3 carbon atoms, or in each case form together with the nitrogen atom a pyrrolidino, piperidino or morpholino group.

6. A process according to claim 1, wherein two mols of thionyl halide of the formula III are used per mol of phosphonic acid of the formula II.

7. A process according to claim 1, wherein the molar ratio of phosphonate of the formula II to thionyl halide of the formula III is 1:2.2 to 2.5.

8. A process according to claim 1, wherein 2.2 to 2.5 mols of thionyl chloride and 0.005 to 0.05 mol of dimethylformamide are used per mol of phosphonate of the formula II, and the reaction mixture is held at reflux temperature until the reaction has finished.

* * * * *